United States Patent
Wells et al.

(10) Patent No.: US 6,783,508 B1
(45) Date of Patent: Aug. 31, 2004

(54) MOXA AND OTHER MEDICAMENT APPLICATION DEVICES FOR DELIVERY OF HEATED MOXA OR OTHER MEDICAMENTS AND FOR USE TO DELIVER PRESSURE AT ACUPUNCTURE POINTS

(76) Inventors: Margery Ann Wells, 1449 Grand Ave., St. Paul, MN (US) 55105; Michael B. Atlass, 3543 Humboldt Ave. South, Minneapolis, MN (US) 55408

( * ) Notice: Subject to any disclaimer, the term of this patent is extended or adjusted under 35 U.S.C. 154(b) by 0 days.

(21) Appl. No.: 09/449,393

(22) Filed: Nov. 26, 1999

(51) Int. Cl.[7] .............................................. A61M 37/00
(52) U.S. Cl. ...................... 604/24; 604/291; 604/290; 607/96; 606/204
(58) Field of Search ............................ 604/19, 20, 22, 604/289–291, 304, 307, 24; 424/40, 41, 125, 447, 725.1, 725; 606/204; 607/96; D24/200, 206, 211

(56) References Cited

U.S. PATENT DOCUMENTS

| | | | | |
|---|---|---|---|---|
| 3,946,733 A | * | 3/1976 | Han ........................... | 126/204 |
| 4,763,657 A | * | 8/1988 | Chen et al. .................... | 607/96 |
| 5,358,483 A | * | 10/1994 | Sibalis ......................... | 604/20 |
| 5,421,816 A | * | 6/1995 | Lipkovker .................... | 604/20 |
| 5,904,664 A | * | 5/1999 | Kim ............................. | 604/19 |
| 6,253,104 B1 | * | 6/2001 | Jo ................................ | 604/20 |
| 6,355,025 B1 | * | 3/2002 | Phipps et al. ............... | 604/501 |
| 6,377,848 B1 | * | 4/2002 | Garde et al. ................. | 604/20 |

* cited by examiner

*Primary Examiner*—Brian L. Casler
*Assistant Examiner*—Jennifer Maynard

(57) ABSTRACT

A device which can hold a position over a particular point, preferably an acupuncture point, on a living body, has particularizeable plugs for performing different treatments to those points. Fixation to the body surface is preferred for treatment using the device is preferred. In most forms, the device will have a channel for accomodating and holding the therapy delivery devices. Moxa or other medicaments can be delivered using the inventive structures, as can pressure, or other force, and the devices can be used to provide heat, magnetism, or other forms of energy amenable to use in the inventive device, and which may be of interest in the oriental medicine and new age therapies of non-standard western medical practices.

3 Claims, 10 Drawing Sheets

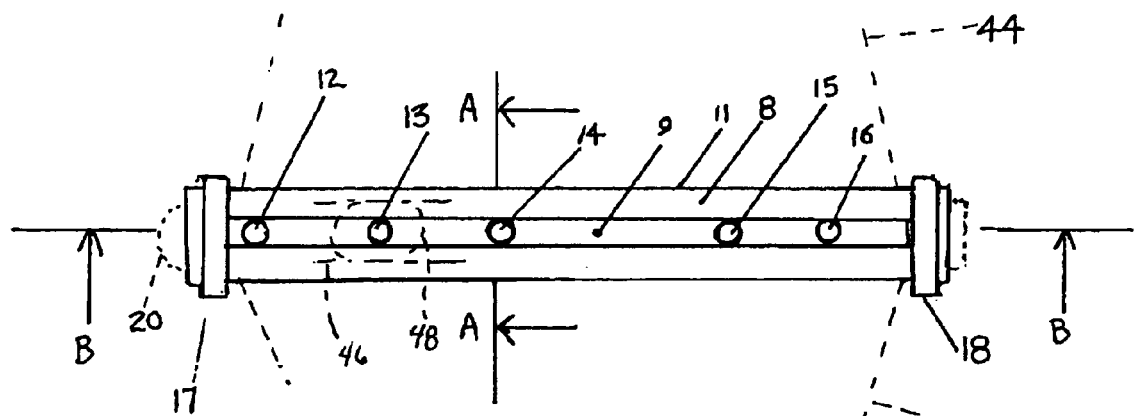
FIG. 1
FIG. 2
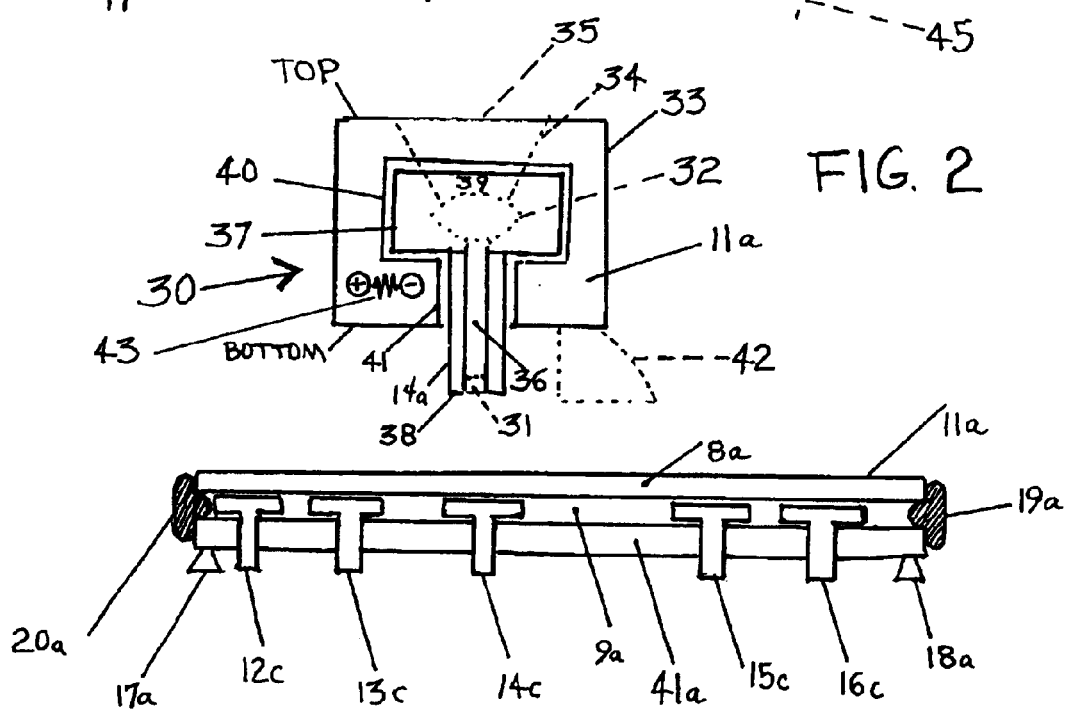
FIG. 3

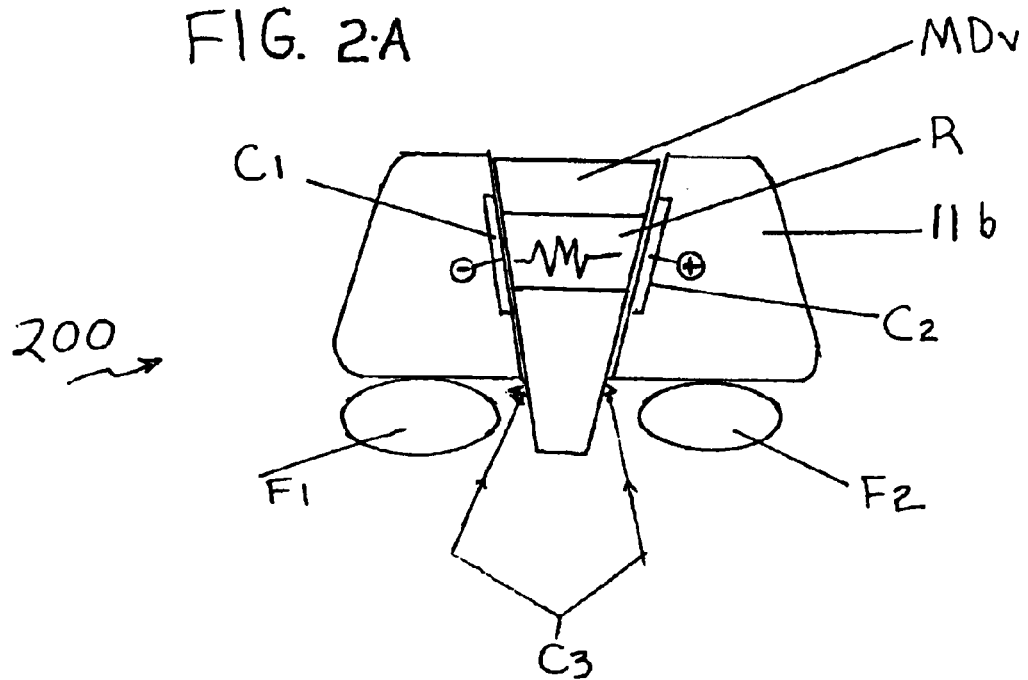
FIG. 2·A
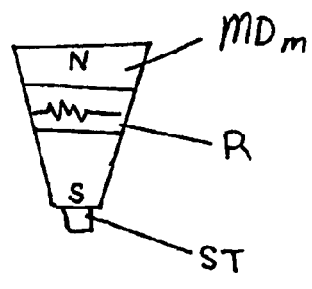
FIG. 2·B
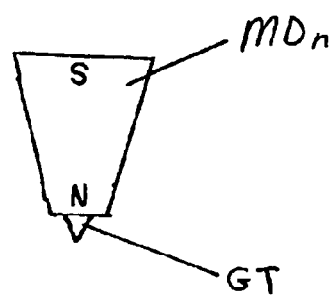
FIG. 2·C

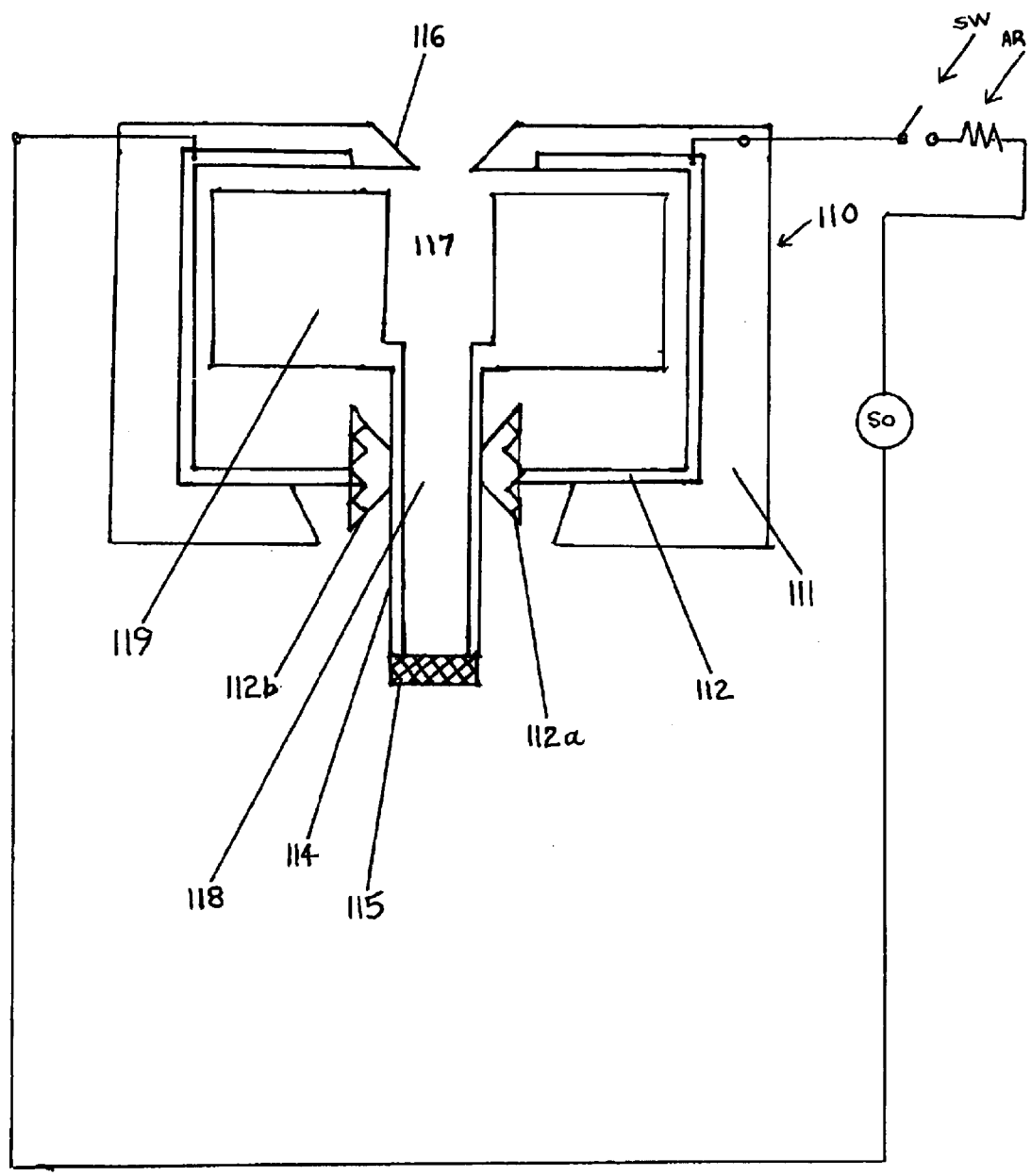

MOXA AND OTHER MEDICAMENT APPLICATION DEVICES FOR DELIVERY OF HEATED MOXA OR OTHER MEDICAMENTS AND FOR USE TO DELIVER PRESSURE AT ACUPUNCTURE POINTS

This application relates to the construction and use of devices for delivery of moxabustion or medicaments in general and particularly to devices for making use of moxabustion or other medicaments easier. It also relates to the use of continuous pressure delivery at acupuncture-type/shiatsu points.

BACKGROUND

Moxabustion is a well known therapeutic agency commonly used in the practice of the forms of medicine derived from ancient Chinese culture, commonly thought of as acupuncture or Traditional Chinese Medicine and also known as Traditional Oriental Medicine, called TCM or TOM herein. Particular formulations of the herb Mugwort are known and currently used by burning it against the skin of a patient where the delivery of heat and "moxa" is thought to be desirable by the acupuncturist. While it is certainly possible to employ other medicaments for therapy in the same manner as Moxa is applied, the most common herbal concoction burned near the skin of someone under treatment is called Moxa, so the treatment is generally referred to as moxabustion. ("Medicaments" as used this document can cover any herbal or oil or mixture of use in "Traditional Chinese" or oriental or other medical practices).

A brief mention of the use of Moxa is made in THE FOUNDATIONS OF CHINESE MEDICINE, By Giovanni Maciocia, published copyright 1989 and reprinted through 1998, page 463 and 464 where the author suggests that the Zhongwan Ren 12 point be used for tonifying stomach and spleen Chi especially in combined with Stomach-36. He states that "Nt is the best point to use, particularly with moxa, for Empty-Cold patterns of the stomach and Spleen. This could be used directly on the point with moxa cones, or the point can be heated with a moxa stick, or a "moxa box" can be applied on the area around the point." He then describes a moxa box. A perhaps modern version of something like a moxa box is found described in U.S. Pat. No. 4,203,438.

Mainly perhaps due to to efforts of Tae Woo Yoo, a form of acupuncture known as Korean Hand Therapy has started to be practiced in America. In this form of acupuncture the traditional acupuncture points are translated or referred to points the hands of the patient, and the hand points are stimulated rather than or in conjunction with the body points. The Ren channel runs down the center of the palm in this system and the tip of the second finger is the equivalent of the patient's face, where the Ren channel will meet the Du Mai channel that will run down the back of the hand. The first and third finger are arms and the little finger and thumb are the legs.

There are also other referent systems (also called "microsystems") that are taught in other medical practices focusing on feet, hands, ears, face, head or even the nose.

It is to be understood that the invention herein can be used with any traditional system or with any referent system (or micro-system) as the practitioner desires or finds useful. The Korean Hand Therapy system (also known as the Koryo Hand Therapy system, and a similar system is referred to as Su Gi(pronounced suu gee)) is described herein first because it provides the most practical first use of the first envisioned embodiments of this invention. This invention can also be used to supplement the or traditional whole body systems as will become apparent in the detailed description.

The application of moxa formulations has been adapted to the Korean Hand Therapy by Dr. Yoo in his inventions described in U.S. Pat. Nos. 5,549,960 and 5,487,883, incorporated by this reference for their disclosure in their entireties. In the use of these devices, it has been found that the regulation of the time of moxa application and the accuracy of patient use of the devices is not always optimal. Further there is a difficulty in getting American patients to burn little sticks stuck to their hands (let alone stuck to other parts of their bodies).

Accordingly, an improvement that could avail the patient of an easy way to apply moxa to him/herself outside the presence of the practitioner, would be quite helpful. It would be more helpful still if the positioning of the moxa delivery could be done with accuracy and ease. Further it would be of benefit if the moxa delivery system could deliver moxa to multiple points at one time. Still further it would be of benefit if the moxa delivery system could deliver heated moxa without the need of burning a flame, striking a match and so forth. Yet further it would be advantageous if a moxa delivery system could deliver a regulated and/or adjustable amount of heat, and even further if that could be done on a timed basis.

The same or a similarly constructed device may be used to deliver pressure alone, without the moxa. A construction allowing a plurality of points to be activated by pressure continuously is formed by the construction described herein for the delivery of moxa, but it may be simplified if used only for the delivery of pressure. (Delivery of pressure may of course be supplemented with tonifying or sedating herbs or by application of gold or silver contact points as will be described within in greater detail with reference to preferred embodiments). For such use a bar may be substituted for the channel containing fixture and points may be secured in any manner along the bar as desired. The bar can then be strapped to the patient in position as desired, activating each of the points by the pressure of the strap. For this construction too, Tae Woo Yoo's patent on a moxabusting implement, U.S. Pat. No. 5,549,960, and Shie's Moxa burner mount for multiple moxa burners, U.S. Pat. No. 4,203,438 may be the closest prior art, and are hereby incorporated by this reference in their entireties. Good Medical (a Korean company) provides a commercially available example of the moxabusting implement described in the Yoo patent. Similar products for sticking burning moxa or other medicament formulae to the skin of a patient can be found for example in the Ibuki Moxa forms of Chosei-kyu and Urashima from the company OMS Medical Supplies of Braintree, Massachusetts.

For either of these devices or the Good Medical form of stick on device, practitioners recommend using various skin shields so as not to burn the patients. These shields are placed on the skin first and disperse the heat. An example is also found in the OMS Medical Supplies catalog and called Kyu-ten-shi. Thus a layer of dispersal material is placed on the point, the layer stuck to the point with adhesive, and the adhesive stick on moxa device stuck to the layer of dispersal material. Therefore it is clear that it is difficult to regulate the heat applied to the skin through the use of these simple stick-on devices and that some easier to control device is needed.

The inventive structures taught in this application can be applied to healing surgical wounds and procedures by providing chi channel reconstructive tools for the practitioner of TOM.

Toward any or all of these improvements this invention is hereby disclosed.

SUMMARY OF THE INVENTION

The invention is a new method and apparatus for delivery of moxa, or for delivery of any of the cornucopia of herbs which may be applied with heat or burning. It provides a point delivery rod through which the heat and/or moxa can be delivered, held in a fixture which can be held firmly in a fixed relationship to the patient's body. Preferably a resistive heater is disposed so as to provide heat either directly or indirectly to the rod and the moxa or other substance that contacts or is held near to the body acupuncture point (or points) of interest. Herbal oils or extracts can also be released through the pores or channels or applied directly to the skin before and during the use of these appliances if desired.

In one preferred embodiment a head structure is attached to the rod and the head and rod assembly is moveable within a channel. The channel may contain a plurality of head and rod assemblies. The channel may be straight or curved, or bent as desirable for the particular area of application. A standoff or standoffs may be provided to stabilize a fixture containing the channel above the skin of the patient. Setscrews or top screws, wing nuts, or other common movement limiting means and structures may be provided to hold the head and rod assembly in a certain location within the channel, or the channel itself may be compressed to hold the head and rod assemblies at chosen locations within the channel, or compression of the fixture and its standoffs against the skin may be used to hold the assemblies in place.

Preferably, either the space around the rod or the center of the rod provide egress of moxa (or other medicaments) to the skin during heating. The body of the rod and the head may contain a moxa passage channel of various forms of construction. The fixture channel may be sealed and contain the moxa itself.

The moxa (and/or various herbs and herbal formulations) may be in any form but powdered or liquid form are most commonly used. In one embodiment the moxa or other substance can be delivered in pre packaged forms for insertion into the head and rod assembly. This assembly can be called a delivery device, or a plug, and may not look like a rod and head if desired.

The tip of the rod may contain a porous ceramic area to allow the moxa to move through it or it may be open if desired. Alternatively it may be made of a stone, preferably porous or marble which can be heated and simply dipped into a liquid moxa solution or oil preparation.

The rods may alternatively provide points of pressure (or polarization) rather than moxa delivery means for some forms of therapy. For this purpose they may be heat-insulated from the fixture if the rest of the rods will be used for moxa delivery, or not if a combined therapy is desirable. They may advantageously be coated in silver or gold and may have a relatively sharp point at the end to contact the skin. Alternatively the tips of various sizes and shapes may be changeable metal tips or have flecks of metal or moxa on them. Also, polarization through the use of magnetic fields, whether through the inclusion of permanent magnetic material or electromagnets may be advantageously employed for selective tonification or sedation of the point of contact in any embodiment mentioned herein where they employ other forms of tonification or sedation through contact. Because magnets have fields that extend beyond themselves, if magnetic fields are used, the fixtures may be positioned above the surface if desired. For a short-handed word to comprise all these applications, the word "force" may be used to include such concepts as polarization, heat, pressure, medicament delivery, and so forth.

Although the first embodiments are designed for human use, application to animals is certainly expected.

BRIEF DESCRIPTION OF THE DRAWINGS

FIG. 1 is a top view of a fixture in accord with a preferred embodiment of the invention.

FIG. 2 is a cross sectional view taken at line A—A of FIG. 1.

FIG. 2A is a cross sectional view of an alternative embodiment.

FIGS. 2B and 2C are alternative forms of plugs for use in places in the inventive devices where medicament delivery devices may also be located.

FIG. 3 is a cross sectional view taken at line B—B of FIG. 1

FIG. 11 is a cross section of an alternative embodiment.

DETAILED DESCRIPTION OF THE PREFERRED EMBODIMENTS

Figure 4:
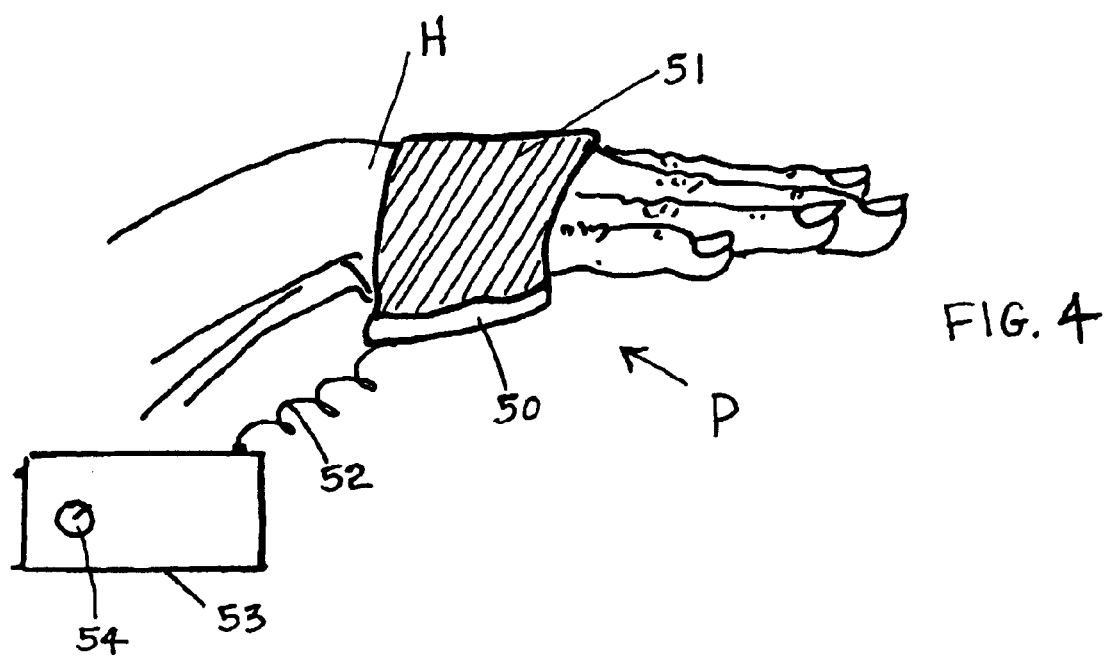
FIG. 4 is an illustration of a preferred embodiment of the invention strapped to a hand of a patient.

Refer first to FIG. 1 in which a basic fixture and strap device 10 is shown having two component straps 44 and 45 and standoffs 17 and 18. The straps are for holding the fixture itself 11 against the skin so that the point delivery devices, here rods 12–16 may be held with whatever pressure the strap may provide against the skin. A typical installation is pictured in FIG. 4, with the holding strap 51, which may be of rubber, elastic, a velcro closer, a watch band like strap with a clasp made or leather or any other form commonly used or known to hold things against a wearer, presses the fixture 50 against the palm. A bendable metal ring or bracelet like the serpentine metal ring form shown in U.S. Pat. No. 5,792,175, incorporated herein by this reference, may also be used to stabilize the holder of the dispensing device(s) around a part of the body, if desired.

In preferred embodiments the device may be stabilized so that the pressure is directed via a perpendicular vector against the skin of the user by use of standoffs, like 17 and 18. These could run lengthwise rather than cross-wise to the length of the fixture as shown, or may even surround the entire fixture as might a pad with a hole or slot in it to pass the lengths of the rods 12–16 for direct contact with the patient's skin.

In any of the structures shown, the addition of a base(not shown in this figure) for spreading the heat may be employed at the point where the rod comes closest to contacting the skin.

In cross section, in FIG. 2, one rod 14a is seen extending from a head member 37 through the opening 41 in the fixture 33. The channel 40 thus contains the head end of the applications member, the rod 14a. The channel is made within the body 11a of the fixture 30. At the side opposite the skin side, side Top, a hole or beveled edge 35/34 may be provided to the channel. This may be used to the provision of a top mounted screw (not shown) for holding one of the head and rod assemblies in place securely within the channel, by mating with a screw channel 39 in the top of the head member. Advantageously, the head member will be provided with a chamber for containing the moxa preparation or medicament 32, which should communicate with the channel 36 in the rod 38. An opening at 31 in the rod 38 is provided to allow the passage of heated moxa or medicament essence to the skin. This opening may be just that, or it may be plugged with a substance known to pass the essence of the moxa preparation to the skin, such as porous ceramic, or a porous metallic mass may be used. It is known that silver metallic or gold metallic points held against the skin have a tonifying or sedating property, and these properties can be taken advantage of if a delivery device has a tip with tonifying or sedating properties built into it. Likewise, in the use of a set of these devices, one may employ devices of similar size and shape to the medicament delivery devices in the fixture to perform tonification or sedation on certain points even without the delivery of medicaments. Thus, the fixtures described herein can be adapted to provide point pressure for sustained periods even without being used to deliver medicaments, or used in conjunction with the medicament delivery devices to provide a therapy that encompasses both forms of stimulation.

The height of a standoff relative to the length of the rod that protrudes from the bottom side (labeled Bottom) of the fixture should be carefully controlled so that the application of pressure is appropriate to the treatment. For example, if desired, the rod ends may be slightly above the surface of the skin allowing for a greater temperature than if they were held against the skin directly. Or, one might desire to provide point pressure against the skin without moxa and thus the rod should extend beyond the lower edge of any standoff used, such as that outlined at 42. Likewise one might prefer to hold the opening 31 against the skin and in such case it would be useful to allow the compressed height of the standoff to be less than the extension of the rod.

Items 17a and 18a could be turn screws or other similar items for adjusting the height of the fixture from the surface of the skin. Typical applications for such devices are found for leveling refrigerators and stoves, but here, obviously, the turn screw devices would have to be much smaller, since the fixture, if it is used on the hand will be too small to accommodate even two of these whereas it would be advantageous to have at least 3. Alternatively sticky tape backed standoffs of various heights can be supplied in a kit and applied as desired. In any event, a material with low heat transfer characteristics should be used.

Standoffs can be of elastomeric or compressible material preferably, but if the exact height off the skin is important, harder materials should be used. Wood or rubber are two preferred substances but any relatively inert substance could be used. Nylon screws may be easiest to use.

An alternative form of channel 11b, having an alternative Medicament delivery device MDv is illustrated in FIG. 2A. In this structure, the standoffs F1 an F2 provide distance from the surface of the patient also. The big difference here is that the medicament delivery device MDv has a resistive strip which will heat up the medicament delivery device when current flows between the positive contact C2 and the negative contact C1 mounted on the interior of the channel 11b. The simpler design of this structure 200 may provide additional benefits as well, in that the medicament delivery device may simply be wedged into the channel and through the use of optional compressible stops, be firmly held into place without additional locking or fixing mechanisms. The medicament delivery device here too may be of burnable material in the upper part which allows for easy removability of the entire delivery device MDv after use due to the reduction of medicament materials due to combustion.

Also, if magnets were to be of interest in a particular therapy, with or without heat, alternative plugs (MDm, MDn, in FIGS. 2B and 2C, respectively) which do not deliver medicaments may be used over the selected point. A gold tip or silver tip (plated or solid) may be employed to help establish the tonification or dispersal of chi mechanism desired for the point. If heat is desired, a restive strip may be included around the plug MDm.

In the embodiment illustrated in FIGS. 1 and 3, a plug is shown at each end of the channel (19, 19a, 20, and 20a). This could be a screw or a rubber plug, or one could manufacture the channel containing fixture with a single end cap, or even leave the ends open, as preferred by the manufacturer.

In the simplest form the channel containing portion 11 is manufactured of metal, the head and rod assemblies are made of ceramic and a plastic screw with a sticky end for contacting and holding the head and rod assembly in the channel are provided. The rod and head assemblies in such a device are pre built, already containing the moxa in the internal spaces of the assembly. The practitioner needs merely to insert the assemblies into the fixture's channel, position them so as to be in the proper relative location when contacting the patient's skin, and then to place the sticky plastic top over the opposite side of the channel from the rod end. For an example see FIGS. 9 and 10, where the plug or cap 89 for holding the rod and head assembly in the channel 11c is shown a screw threads set 84 and 88 may provide the means for pressing the plug against the head or these fins 88 may be compressible plastic ridges which will force the end 89 against the head with pressure. Alternatively the surface 89 may have a glue containing area. Preferably, surface 95 will have a glue or sticky surface on the underside of cap 94.

Figure 12:
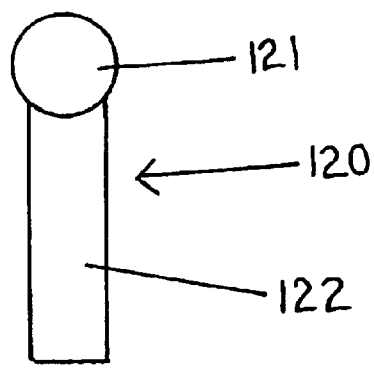
FIG. 12 is a cross section of a pre formed load for use with the embodiment of FIG. 11.

An alternative form of the device can be seen in FIGS. 11 and 12. IN this form a load of compressed moxa material 120 is preformed to be inserted into opening 116 of the fixture 111 formed of an inert material, so that it can rest snugly within the opening 117 and 118 of the delivery device 119. Here Nichrome wire is forming a compressible interface with the outer surface of the shaft 114 of delivery device 119 so that when current is delivered from the source So across the adjustable resistance AR and the closed switch SW, the copper raceways 112a and 112b can provide substantial heat to the load in area 118. Again in this embodiment we prefer to provide a slightly porous and non heat conducting tip 115 for contact with the skin to prevent scaring burns.

In FIG. 4, a preferred fixture 50 with the moxa delivery devices inside loaded with moxa (not shown) is strapped to the palm P of a hand H by a preferably elastic band 51. This band may be of any material desirable, and could be non-elastic with a variable sized closure mechanism like a buckle or a velcro fastener. The standoffs would provide spacing of the fixture from the skin. The switch and variable power control, which can be the same component and preferably are controlled by a single rotating or slideable switch control 54, are in a conveniently located box 53 connected by a wire pair 52. While the power grid may be used and the unit plugged into a wall socket for power, it is preferred to include a battery power source in the box 53.

Figure 5:
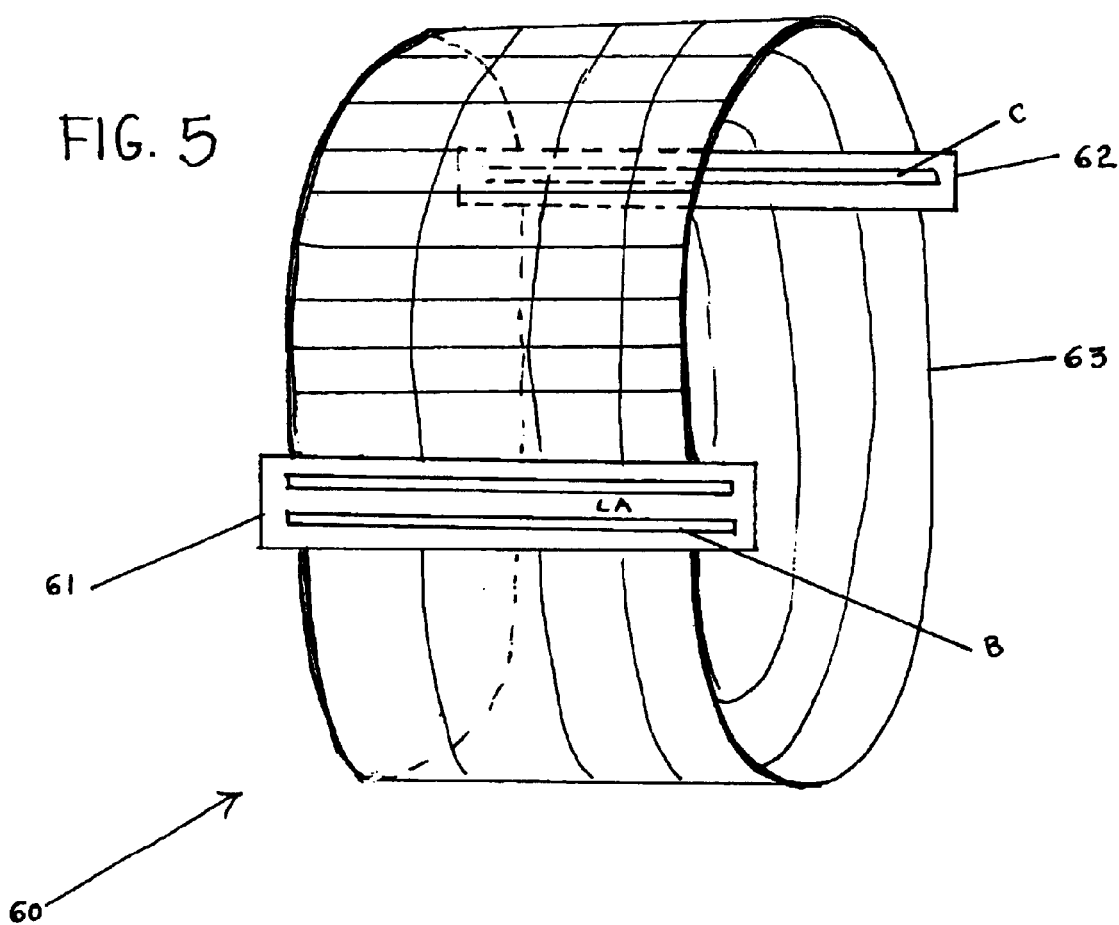
FIG. 5 is an illustration of a preferred embodiment having a plurality of fixtures.

In Koryo therapy, and in other uses of moxa, it may be therapeutically useful to have application to two sides of a body part. Accordingly, the device of FIG. 5 provides for two fixtures 61 and 62 connected by a band 63 to hold the two fixtures on opposite sides of the body part. Also, a single or double row of moxa delivery devices can be included in the fixtures, as indicated here with fixture 61 having two rows, A and B for holding two rows of fixtures, while fixture 62 is of the form we have been discussing so far. More likely however is the use of a plurality of fixtures greater than two in the band so that the positioning of the rows of delivery devices can be spaced and angled for greatest effectiveness. If the fixtures are formed of bendable materials for the practitioner to shape the surface of the body where used, conformation to the surface of the skin is more positive and a more even application of therapy will result.

The band could be large enough to be fit around the entire trunk of a body, or other lesser sized body parts, for treating rows of points simultaneously, using fixtures of suitable length.

Figure 6:
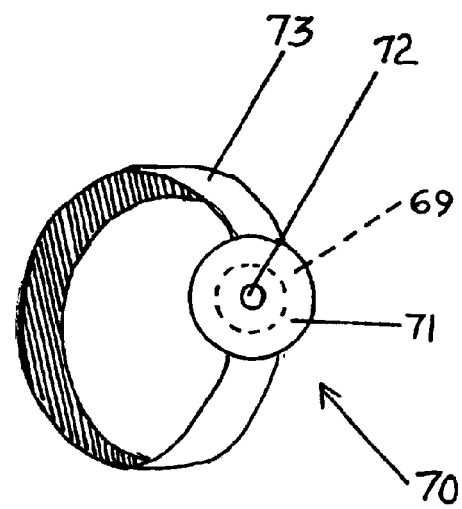
FIG. 6 is an illustration of a preferred embodiment having a single point.

In FIG. 6, the band 73 again is transformed to provide a fixed holding structure for a single moxa delivery device, delivered at a point 72 from the underside of a round fixture 71 holding a head within at outline 69. The power and switch device as shown in FIG. 4 is not shown for any of the embodiments described with respect to FIGS. 5 or 6 but is of course present. It would also be possible to include it on the band (63, 73, or 51) if desired, or even in the fixture itself, depending on the bulkiness and patient acceptance of the configuration.

Figure 7:
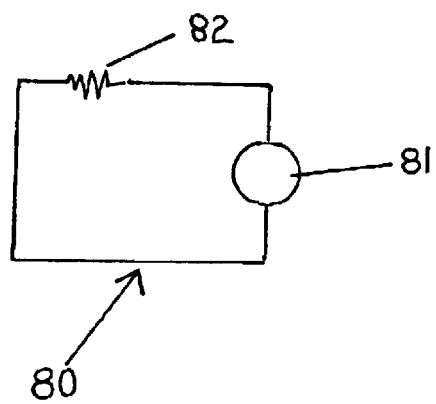
FIG. 7 is an illustration of a simplification of a circuit for use by preferred embodiments of this invention.

A very basic electrical circuit required for the electrical forms of this invention is shown in FIG. 7, being a source 81 and a heat producing resistance 82 for heating the moxa or other substance. Adjustments to the power level to provide comfort for the patient using the moxa is a primary concern however.

Figure 8:
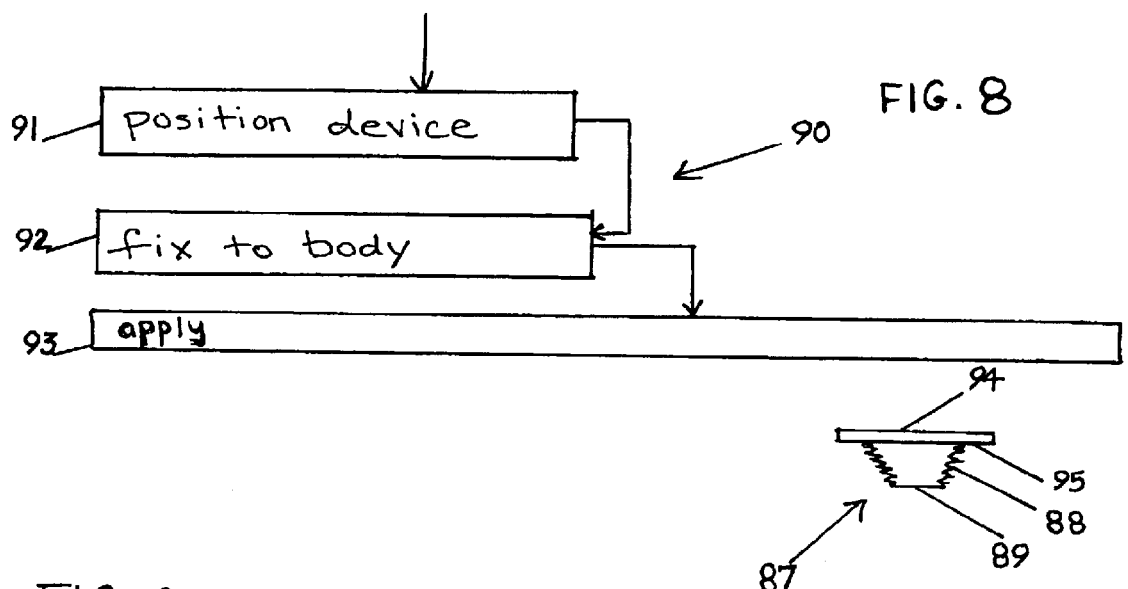
FIG. 8 is a flow chart.

The process of using any of these devices is outlined in FIG. 8 in which the steps are outlined. It is assumed that preceding step 91 that the patient has been indicated to have need for this treatment, of course. Also, the load, if there is one, or the moxa delivery device has been filled with moxa or whichever substance is to be heated in the presence of the patient, prior to step 91.

In step 91 the fixture with the moxa delivery device is adjusted in relative position to each other and locked into said relative position. This position should be on in which each of the devices in a fixture being used is locatable over a point needing treatment while the other devices are located over other points needing treatment.

A test step may be performed to ensure that the devices are heating in their locked positions.

The fixture is then fixed to the body with the band in step 92. It may be tested in this position to see if the patient has one or more points at too high a heat when the power is turned on. Adjustments can be made to the standoffs, if required. It is likely that depending on the condition of the patient there will be different sensations and degrees of heat even with even application of heat and moxa to a plurality of points. Each individual patient will be different.

In step 93 the treatment is applied. With variable power delivering variable heat, the patient or practitioner may adjust the level of heat, the speed of burning and so forth. When a regimen for treatment is agreed to, the patient can be sent home with the fixture and delivery devices fixed within it to treat his/herself until the next practitioner visit. This flexibility in treatment will provide great advantages in treatment timing and effectiveness which would be unavailable in situations where moxa and similar treatments could only be performed with assistance from someone other than the patient.

Figure 10:
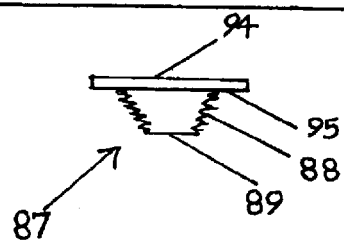
FIG. 10 is a cross section of a cap for use with the channel of FIG. 9.
Figure 9:
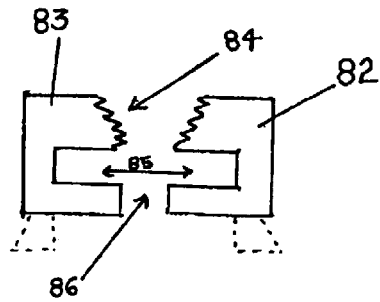
FIG. 9 is a cross section of a channel for use in this invention.

Finally, referring to FIGS. 9 and 10, the fixture 11c is shown again in cross sectional view at some point other than either end. In section it is of two halves 82 and 83 with a raceway 85 for the head of the delivery device to move within and an opening 86 through which the tail of the delivery device can also travel. In this embodiment a set of teeth 84 is provided in the opening opposite opening 86. These will compress cap 87 against the head of a delivery device in the raceway, holding surface 89 there against it with some downward force. Surface 89 may also be provided with a sticky surface if desired. Application of force by a user's finger or thumb against surface 95 of the top ember 95 of the cap 87 will force the teeth 88 under the mating teeth 84 in 11c, thus locking the device underneath the cap into a fixed location within the raceway in the fixture 11c.

Figure 13:
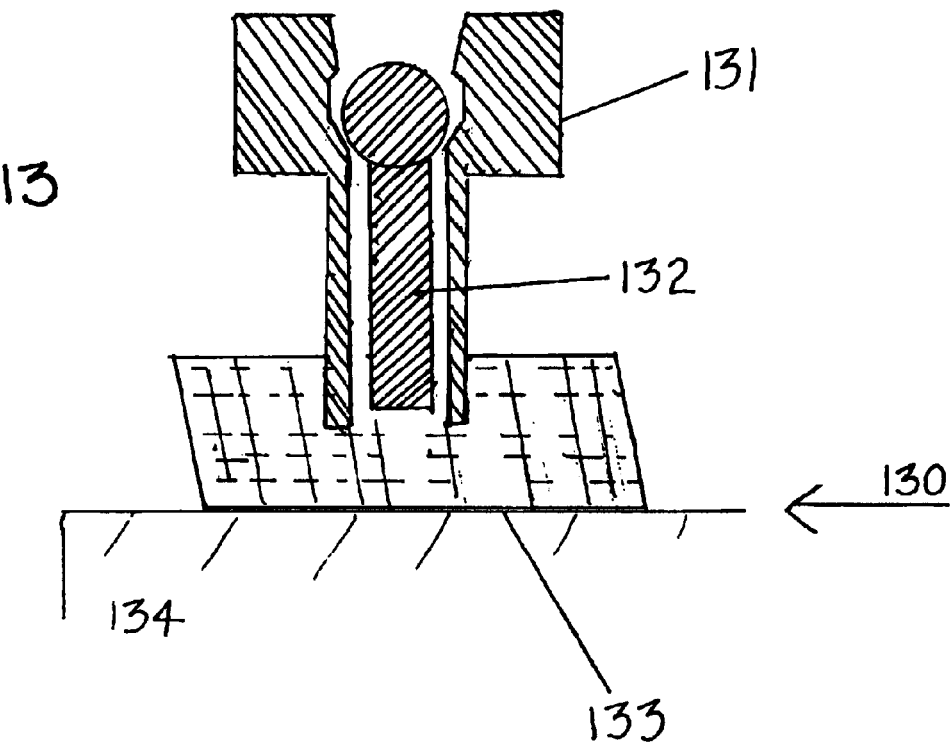
FIG. 13 is a delivery device with heat spreader assembly for use with this invention.

FIG. 13 illustrates another enhancement to the device for those wishing to spread the heat out beyond the point or to provide an extra layer of protection from burning. Here shown is an assembly 130 with a heat spreader 133, preferably formed of a layered material similar to the base of the moxibusting implement of U.S. Pat. No. 5,549,960, allowing the medicament, or moxa from the heated load 132 in the delivery device 131 to pass into the skin 134 of the living body to be subjected to this treatment, when the device is in place.

Figure 14:
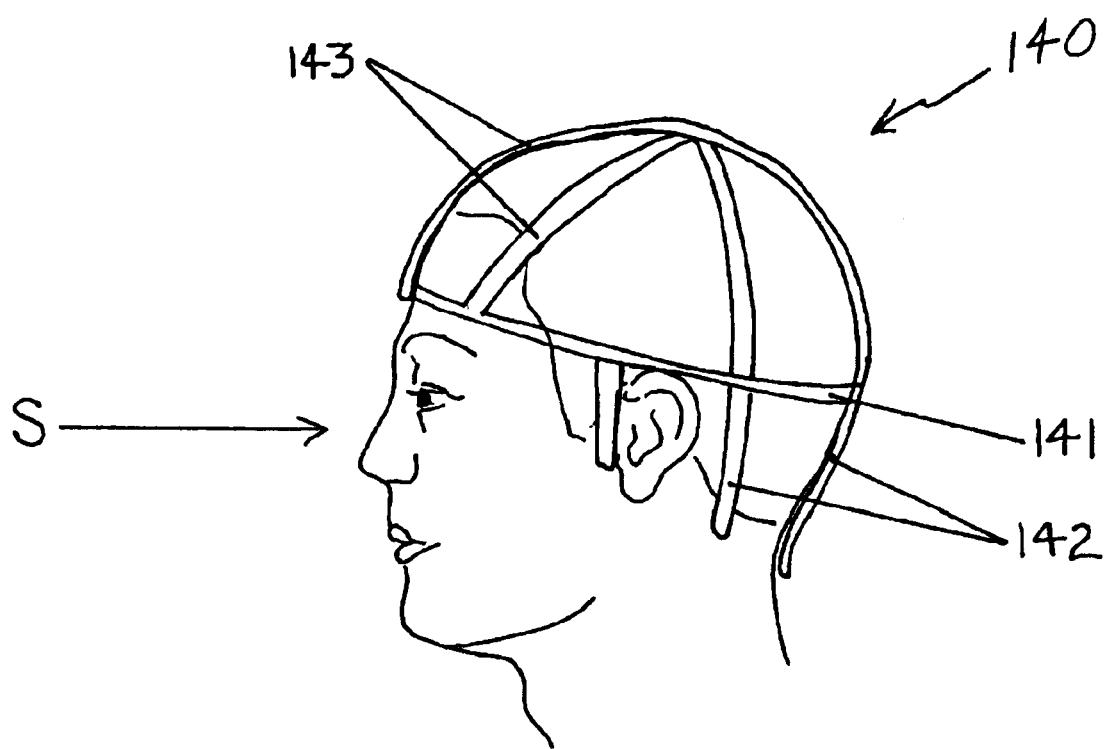
FIG. 14 is a head mounted device in accord with a preferred embodiment of this invention.

An interesting additional preferred embodiment could employ the teachings of Yamamoto-sensei from Japan who would provide treatment to head acupuncture points. Here we refer to FIG. 14 in which a device 140 formed and constructed in accord with the teachings provided in this document are molded to fit on the head of a subject S, having at least one band 141 horizontal to the upright subject and longitninal runs 141 and 143 below and above the circumferential band 141. In such a form, the major acupuncture points of the head described by Yamamoto and others are available to be treated as described herewithin.

Figure 15:
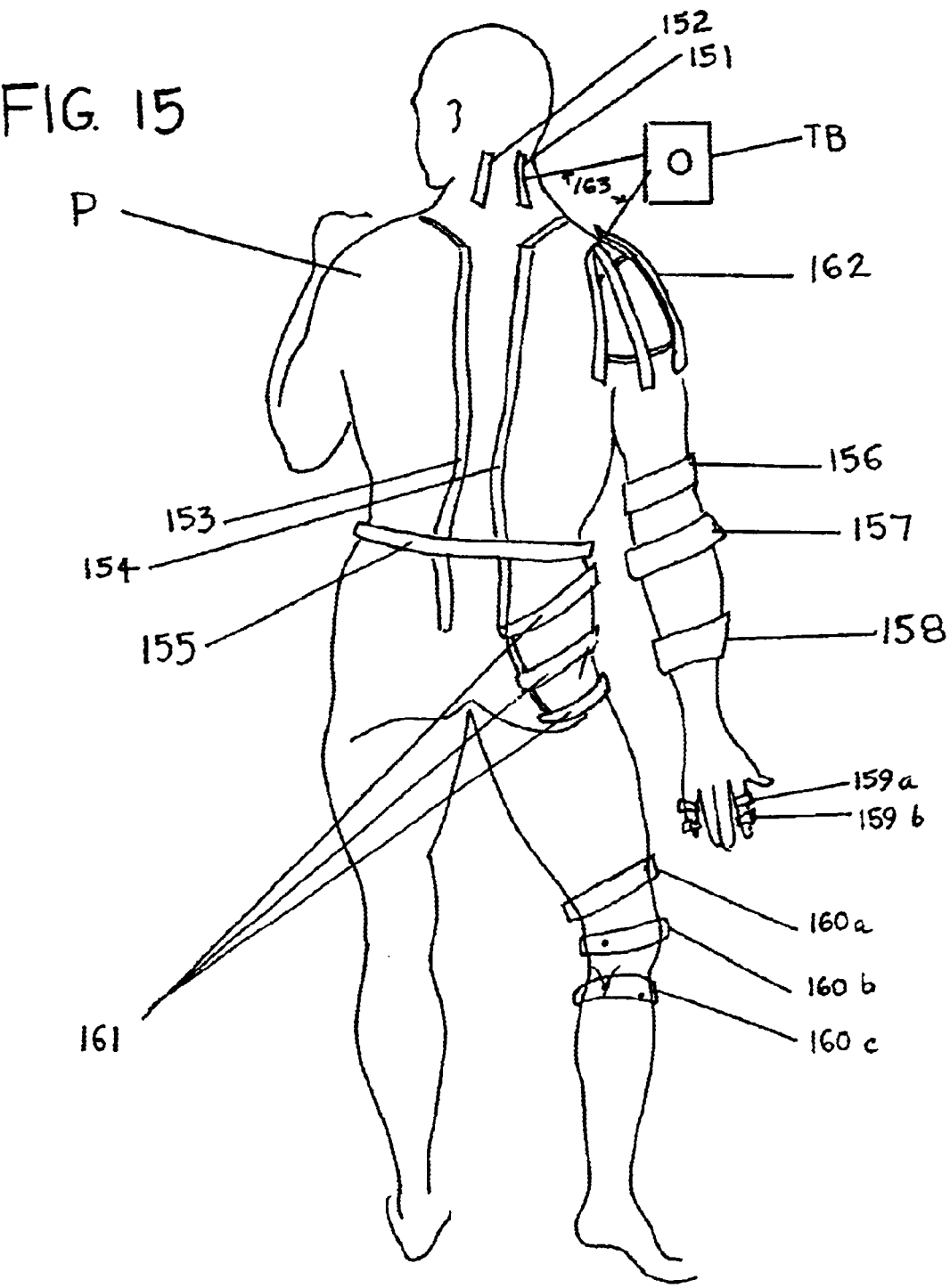
FIGS. 15 and 16 illustrate the use of large embodiments for limbs and trunk and on the body generally in front and back respectively.
Figure 16:
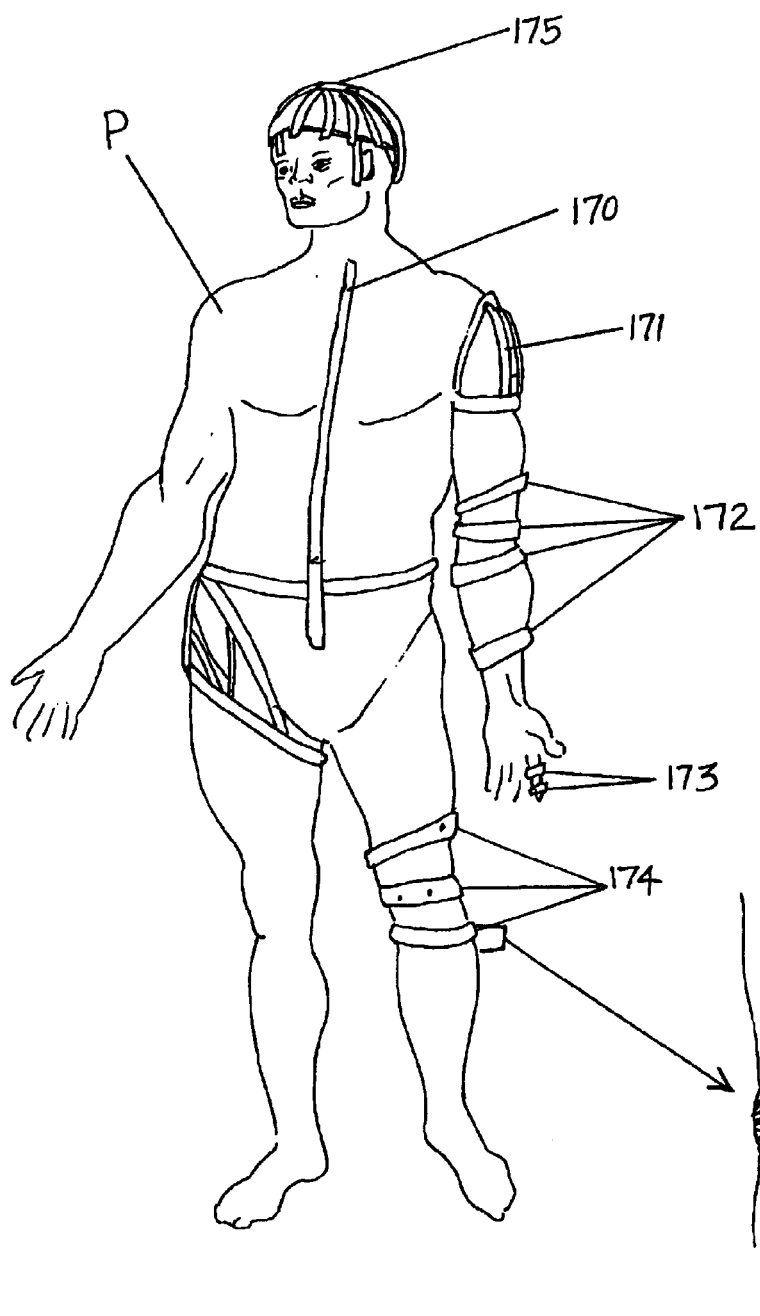
Figure 16A:
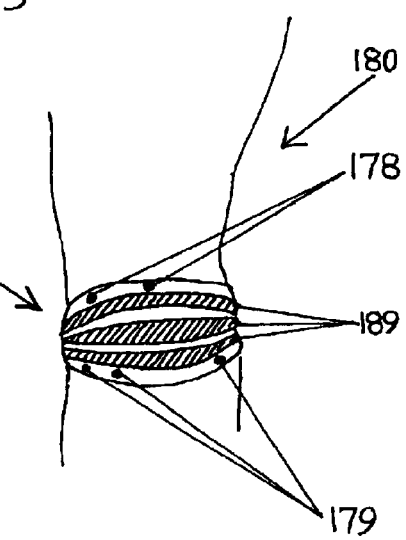
FIG. 16A is a view of embodiments of the invention on a knee.

Expanded capabilities can be made of the invention so far described so as to provide both in clinic practice supplemental devices and devices which can be taken home be the patients. Illustrated in FIGS. 15, 16 and 16A are strips of support structures which may have the raceways or other plug supporting structures and which may also contain the electrical conductors necessary to provide a heat source, or electromagnetic power source to the point where the plug or medicament delivery device may be advantageously located. Thus a patient P, who may advantageously be lying face down on a treatment table, could have strips built in accord with the teachings hereof placed over a portion of a channel (151–155, for examples) and a treatment box TB could supply the power to the strips, shown here supplying power through wires 163 to the single strip 151 and the compound strip 162. Bands could be used around appendages such as 156–159a and 159b to stabilize the strip, which can be closed with velcro or elastic. All of these could be attached to a separate treatment box to deliver electric power if desired. In FIG. 16, the patient is shown with other strip mountings 170–175. FIG. 16A shows an alternative having four strips 181–184 about the knee of a patient with plugs or medicament delivery devices 178 and 179 secured therein. With this multiple strip device 180, a fabric strap 189 holds the strips together in a flexible arrangement around the knee.

Numerous methods and device adaptations can be imagined to lock the delivery devices into fixed points within the fixture including a clamp that brings the two fixture halves in closer proximity, a configuration of the devices themselves that includes threads or teeth as a part of the head, pins that are inserted into holes in the fixture, elastomeric compressible head forms that stay in place once inserted into a groove that substitutes for the raceway, and so on. It is believed that conventional securing devices for holding the delivery devices in position within the groove or raceway of the fixture are within the disclosure's ambit by this discussion.

Thus it has been shown that with flexibility suitable to modern acupuncture, pressure, heat, magnet, gold and silver, heating and application of local medicaments and other treatments, a device can be constructed to assist in clinical TOM practice which, under proper supervision can allow patients to continue such treatments at home. Likewise the scope of this invention is not believed limited in any other way, except as set forth in the following claims.

What is claimed is:

1. A delivey structure for delivering a heated medicamemt or sedating force to specific points on the surface of a living body for a sustained period time comprising:
   a channel containing room for holding in a fixed position within said channel a tonifying or sedating or medicament delivery device, said channel having an opening positionable toward said living body,
   a fixture in which said channel is located for holding said channel in a fixed location against said body whereby said opening is positioned toward said living body when said fixture is holding said channel in said fixed location, and
   at least one plug selectable from a set of tonifying, sedating or medicament delivery devices selectable by a user for being held in said fixed position within said channel, said plug having an end for delivering said force, whereby said end of said plug is held in said fixed position within said channel extends through said opening in said channel for positioning toward said surface of said living body wherein said at least one plug comprises a pair of contacts for connection to electrical contacts on said channel.

2. A delivery structure for delivering a heated medicament or tonifying or sedating force to specific points on the surface of a living body for a sustained period of time comprising:
   a channel containing room for holding in a fixed position within said channel a tonifying or sedating or medicament delivery device, said channel having an opening positionable toward said living body,
   a fixture in which said channel is located for holding said channel in a fixed location against said body, whereby said opening is positioned toward said living body when said fixture is holding said channel in said fixed location, and
   at least one plug selectable from a set of tonifying, sedating or medicament delivery devices selectable by a user for being held in said fixed position within said channel, said plug having an end for delivering said force, whereby said end of said plug is held in said fixed position within said channel extends through said opening in said channel for positioning toward said surface of said living body wherein said at least one plug comprises a resistive heater for connection to electrical contacts on said channel.

3. A delivery structure for delivering a heated medicament or tonifying of sedating force to specific points on the surface of a living body for a sustained period of time comprising:
   a channel containing room for holding in a fixed position within said channel a tonifying or sedating or medicament delivery device, said channel having an opening positionable toward said living body,
   a fixture in which said channel is located for holding said channel in a fixed location against said body, whereby said opening is positioned toward said living body when said fixture is holding said channel in said fixed location, and
   at least one plug selectable from a set of tonifying, sedating or medicament delivery devices selectable by a user for being held in said fixed position within said channel, said plug having an end for delivering said force, whereby said end of said plug when said plug is held in said fixed position within said channel extend through said opening in said channel for position toward said surface of said living body wherein said channel is shaped to admit a plurality of said plugs, at user fixable locations spaced apart from each other at an adjustable distance as set by a user.

* * * * *